US011590258B2

(12) United States Patent
Lee et al.

(10) Patent No.: US 11,590,258 B2
(45) Date of Patent: Feb. 28, 2023

(54) VITAMIN C-CONTAINING POLYCAPROLACTONE MICROSPHERE FILLER AND PREPARATION METHOD THEREFOR

(71) Applicant: G2GBIO, INC., Daejeon (KR)

(72) Inventors: Heeyong Lee, Daejeon (KR); Eunyoung Seol, Daejeon (KR); Kwonhyeok Yoon, Daejeon (KR); Yongha Na, Daejeon (KR)

(73) Assignee: G2GBIO, INC., Daejeon (KR)

( * ) Notice: Subject to any disclaimer, the term of this patent is extended or adjusted under 35 U.S.C. 154(b) by 93 days.

(21) Appl. No.: 16/960,366

(22) PCT Filed: Jan. 10, 2019

(86) PCT No.: PCT/KR2019/000403
§ 371 (c)(1),
(2) Date: Jul. 7, 2020

(87) PCT Pub. No.: WO2019/139380
PCT Pub. Date: Jul. 18, 2019

(65) Prior Publication Data
US 2021/0052768 A1    Feb. 25, 2021

(30) Foreign Application Priority Data
Jan. 10, 2018 (KR) .................. 10-2018-0003584

(51) Int. Cl.
*A61L 27/18* (2006.01)
*A61K 8/02* (2006.01)
(Continued)

(52) U.S. Cl.
CPC .............. *A61L 27/18* (2013.01); *A61K 8/025* (2013.01); *A61K 8/676* (2013.01); *A61L 27/54* (2013.01);
(Continued)

(58) Field of Classification Search
None
See application file for complete search history.

(56) References Cited

U.S. PATENT DOCUMENTS

| 2010/0215702 | A1* | 8/2010 | Super ................ A61L 27/52 424/501 |
| 2012/0015011 | A1* | 1/2012 | Shim ................ A61K 8/11 424/401 |

(Continued)

FOREIGN PATENT DOCUMENTS

| CN | 1976680 | 6/2007 |
| CN | 102429876 | 5/2012 |

(Continued)

OTHER PUBLICATIONS

Amal Amin et al., "Assessment of Formulation Parameters Needed for Successful Vitamin C Entrapped Polycaprolactone Nanoparticles", International Journal of Polymeric Materials and Polymeric Biomaterials, vol. 67, No. 16, Nov. 17, 2017 (Nov. 17, 2017), pp. 942-950, XP055831481.

(Continued)

*Primary Examiner* — Dominic Lazaro
(74) *Attorney, Agent, or Firm* — Lex IP Meister, PLLC (57) ABSTRACT

The present disclosure relates to a polycaprolactone microsphere containing vitamin C, a filler including the same and a preparation method therefor. Provided is a polycaprolactone microsphere filler obtained by encapsulating vitamin C in polycaprolactone microspheres, which, when injected into a living body, exhibits a rapid collagen formation effect as well as a high tissue restoration property and maintains the effects for a long period of time, thereby showing excellent restoration or volume expansion or wrinkle improvement properties of soft tissues such as cheeks, breasts, nose, lips, and buttocks and reducing wrinkles.

16 Claims, 2 Drawing Sheets

Example 1-4

(51) Int. Cl.
  *A61L 27/54* (2006.01)
  *A61K 8/67* (2006.01)
  *A61Q 19/08* (2006.01)

(52) U.S. Cl.
  CPC ........ *A61Q 19/08* (2013.01); *A61K 2800/412* (2013.01); *A61K 2800/91* (2013.01)

(56) References Cited

U.S. PATENT DOCUMENTS

2014/0308362 A1* 10/2014 Bellas .................. A61L 27/58 424/499
2014/0341997 A1* 11/2014 Kim .................... A61K 9/1682 424/489

FOREIGN PATENT DOCUMENTS

| KR | 10-1249716 | 4/2013 |
| KR | 10-2014-0135337 | 11/2014 |
| KR | 10-2016-0107781 | 9/2016 |
| KR | 10-2017-0075070 | 7/2017 |
| RU | 2491096 | 2/2014 |
| WO | 2010-078040 | 7/2010 |

OTHER PUBLICATIONS

Shabbar Abbas et al., "Ascorbic Acid: Microencapsulation Techniques and Trends—A Review", Food Reviews International, 28:343-374, Feb. 21, 2012.

Erhan Ozsagiroglu et al., "Encapsulation of L-Ascorbic Acid via Polycaprolactone-Polyethylene Glycol-Casein Bioblends", Polish Journal of Chemical Technology, vol. 17, No. 4, Nov. 27, 2015 (Nov. 27, 2015), pp. 32-36, XP055831347.

EPO, European Search Report of EP 19738756.6 dated Aug. 19, 2021.

KIPO, PCT Search Report & Written Opinion of PCT/KR2019/000403 dated Apr. 19, 2019.

Modern Cosmetics: Science and Technology (vol. 1), Bingyi Qiu, Zhihong Gao edited, China Light Industry Press, pp. 668 to 669, published on Mar. 31, 2016.

SIPO, Office Action of the corresponding Chinese Patent Application No. 201980018358.8., dated May 30, 2022.

* cited by examiner

[FIG. 1a]

Example 1-4

[FIG. 1b]

Comparative example 1-1

VITAMIN C-CONTAINING POLYCAPROLACTONE MICROSPHERE FILLER AND PREPARATION METHOD THEREFOR

TECHNICAL FIELD

Cross-Reference to Related Application(S)

This application claims the benefit of Korean Patent Application No. 10-2018-0003584 filed on Jan. 10, 2018 with the Korean Intellectual Property Office, the disclosure of which is herein incorporated by reference in its entirety.

The present disclosure relates to a vitamin C-containing polycaprolactone microsphere filler and a method for preparing the same, and more particularly, to a vitamin C-containing polycaprolactone microsphere filler which not only has resolved the in vivo stability problems of vitamin C by containing vitamin C therein, but also when applied to a living body, exhibits rapid collagen regeneration and volume increase effects after treatment, and further maintains the effects for a long period of time, and a method for preparing the same.

BACKGROUND ART

Dermal fillers are an injection type medical instrument that injects materials safe for a human body into a dermic layer of face to replenish dermal tissues, such as improving wrinkles and volume in aesthetic appearance, and are used for so-called anti-aging treatments, including botulinum toxin (BOTOX®), autologous fat transplantation, thread lift, microneedle, laser treatment, dermabrasion, and the like.

The first-generation dermal filler that was first developed is an animal-derived collagen filler, and is rarely used in recent years because the duration of effect after treatment is short from 2 to 4 months and it is troublesome that dermal hypersensitivity reaction tests must be performed one month before treatment.

The second-generation dermal filler is a hyaluronic acid filler, and is currently the most frequently used filler in that it has a longer duration of effect than a collagen filler, and has significantly less side effects such as dermal hypersensitivity reactions because it is composed of polysaccharides similar to the components of the human body and thus do not require dermal reaction tests like collagen fillers. In particular, hyaluronic acid is easy to treat and remove, has excellent viscoelasticity, maintains the moisture, volume and elasticity of the skin, which is thus very suitable as a raw material for dermal fillers. Recently, studies have been actively conducted to extend the duration of effect by inducing crosslinking of hyaluronic acid to increase particle size and molecular weight, but since the duration of effect is relatively short from 6 to 12 months, it is troublesome that the treatments must be repeated every 6 to 12 months.

The third-generation dermal filler, which is a synthetic polymer filler such as polylactic acid (PLA) or polycaprolactone (PCL), is very gradually decomposed in the human body, and therefore, is used for the purpose of exhibiting a longer duration of effect as compared with collagen and hyaluronic acid fillers which are absorbent fillers. In particular, polycaprolactone is 100% absorbed by the human body and thus is a safe component, and is advantageous in that it is absorbed more slowly than polylactic acid after being implanted into the skin, promotes the production of collagen, and lasts the effect for 1 to 4 years as a soft-feeling tissue having no foreign matter feeling. However, the polycaprolactone filler is a filler in the form of a microsphere and must be administered by suspending it in a gel carrier such as carboxymethylcellulose (CMC), and shows the effects only after 6-8 weeks after injection into the skin. Thus, this is disadvantageous in that the satisfaction of the treatment is lower than that of the hyaluronic acid filler showing an immediate effect after the treatment.

Meanwhile, it is known that vitamin C or L-ascorbic acid, its derivatives and salts enhance the immune function of the human body, promote the production of collagen, and exhibit the effect of maintaining or enhancing the production of hyaluronic acid, whereby they exhibit an anti-aging effect that prevents or improves skin wrinkles, fine lines, freckles, and laxity with aging. However, there is a problem that vitamin C is very unstable both inside and outside the living body, reacts sensitively to the external environment such as air, especially oxygen, heat or light and is easily decomposed by oxidation. Thus, it is a fact that vitamin C is used restrictively in cosmetics and the like for the purpose of forming collagen and improving wrinkles by utilizing stabilized forms such as various derivatives.

Therefore, there is a need to develop a new polycaprolactone microparticle filler with improved efficacy by solving the in vivo stability problem of vitamin C by utilizing the properties of the existing polycaprolactone microparticle filler and encapsulating vitamin C with polycaprolactone microspheres.

DETAILED DESCRIPTION OF THE INVENTION

Technical Problem

The present disclosure has been devised to resolve the above-mentioned in vivo stability problems of vitamin C and improve the efficacy of the polycaprolactone microsphere filler, and it is an object of the present disclosure to provide a vitamin C-containing polycaprolactone microsphere which, when applied to a living body, rapidly exhibits effects after treatment and maintains the effects for a long period of time, and a filler comprising the same and a method for preparing the same.

Technical Solution

In order to achieve the above objects, one aspect of the present disclosure provides a polycaprolactone microsphere comprising 0.01 to 6.5% by weight of vitamin C based on total 100% by weight of the polycaprolactone microsphere containing vitamin C and having an average particle size of 10 to 100 µm.

In another aspect of the present disclosure, there is provided a method for preparing a vitamin C-containing polycaprolactone microsphere, comprising the steps of: (a) preparing a dispersed phase by dissolving polycaprolactone in a first solvent and dissolving vitamin C in a second solvent to prepare each solution, and then uniformly mixing the two solutions to prepare a single solution; (b) preparing an emulsion by mixing the dispersed phase with an aqueous solution (continuous phase) containing a surfactant; (c) forming a microsphere by extracting and evaporating organic solvents from the dispersed phase into a continuous phase in the emulsion prepared in step (b); and (d) recovering the microsphere from the continuous phase of step (c).

According to yet another aspect of the present disclosure, there is provided a filler comprising the vitamin C-containing polycaprolactone microsphere of the present disclosure;

and a pharmaceutically acceptable aqueous carrier and a polycaprolactone microsphere.

Advantageous Effects

The filler comprising the vitamin C-containing polycaprolactone microsphere according to the present disclosure not only exhibits a rapid collagen formation effect when applied to a living body and exhibits a high tissue restoration property, but also maintains the effects for a long period of time, thereby showing excellent restoration or volume expansion of soft tissues such as cheeks, breasts, nose, lips, and buttocks, or wrinkle improvement properties.

DETAILED DESCRIPTION OF THE EMBODIMENTS

Hereinafter, the present disclosure will be described in more detail.

As used herein, the "vitamin C" is used as generic term that collectively refers to not only L-ascorbic acid but also its derivatives and salts. Vitamin C may be selected from the group consisting of L-ascorbic acid, sodium ascorbylphosphate, magnesium ascorbylphosphate, calcium ascorbylphosphate, ascorbic acid polypeptide, ethyl ascorbyl ether, ascorbyl dipalmitate, ascorbyl palmitate, ascorbyl glucoside and ascorbyl ethylsilanol pectinate, but is not limited thereto. Preferably, L-ascorbic acid can be used.

In one embodiment, the amount of vitamin C encapsulated in the vitamin C-containing polycaprolactone microsphere of the present disclosure may be 0.01 to 6.5% by weight, preferably 0.02 to 6.0% by weight, based on total 100% by weight of the microsphere. This amount of encapsulation is optimized such that the characteristic physiological activity of vitamin C can exhibit a synergistic effect at the injected site while ensuring the in vivo stability of vitamin C.

The present disclosure is characterized in that such vitamin C is encapsulated in the polycaprolactone microspheres and used together as a filler, thereby promoting various biological functions such as hyaluronic acid production and collagen synthesis.

The vitamin C-containing polycaprolactone microsphere of the present disclosure is prepared using polycaprolactone in which an inherent viscosity of polycaprolactone, which is a biodegradable polymer, is 0.16 to 1.90 dL/g. The inherent viscosity of polycaprolactone used herein refers to the inherent viscosity measured in chloroform at 25° C. using a Ubbelohde viscometer. Examples of the above polycaprolactone polymer include Resormer C209, C212 and C217 available from Evonik, Purasorb PC02, PC04, PC08, PC12 and PC17 available from Corbion, and the like.

The vitamin C-containing polycaprolactone microsphere according to the present disclosure has an average particle size of 10 μm or more and 100 μm or less, for example, preferably 10 to 30 μm, 10 to 50 μm, or 10 to 100 μm, 20 to 50 μm, 30 to 60 μm, or 40 to 70 μm. The average particle size used herein refers to a median diameter as the particle size corresponding to 50% of the volume % in the particle size distribution curve, and is represented by D50 or D (v, 0.5).

When the average particle size of the vitamin C-containing polycaprolactone microsphere is less than 10 μm, it may be phagocytosed by macrophages when administered in the living body. When the average particle size is larger than 100 μm, the injectability is decreased when injected with a syringe, and the injection needle becomes thicker, causing more pain during injection, which is not preferable.

Preferably, the vitamin C-containing polycaprolactone microsphere according to the present disclosure has a uniform particle distribution. The microsphere having a uniform particle distribution has less deviation in the residual amount during injection and less clogging phenomenon as compared with a non-uniform microsphere, and thus, a fine injection needle can be used. Preferably, the size distribution degree or span value of the polycaprolactone microspheres of the present disclosure is 1.0 or less. More preferably, the size distribution is 0 or more and 0.8 or less. The size distribution or span value used herein is an index indicating the uniformity of the particle size of the microsphere, and means a value determined by the formula of the size distribution (span value)=(Dv0.9−Dv0.1)/Dv0.5. Here, Dv0.1 means a particle size corresponding to 10% of the volume % in the particle size distribution curve of the microsphere, Dv0.5 means a particle size corresponding to 50% of the volume % in the particle size distribution curve of the microsphere, and Dv0.9 means a particle size corresponding to 90% of the volume % in the particle size distribution curve of the microsphere. The vitamin C-containing polycaprolactone microsphere according to the present disclosure is characterized by exhibiting a uniform size distribution while exhibiting a particle size of 10 μm or more and 100 μm or less, thereby reducing needle clogging and improving injectability. The particle size range and span values as described above are optimized so as to include the amount of encapsulation that allows vitamin C in the polycaprolactone microsphere to be eluted in an appropriate amount for a long period of time.

The vitamin C-containing polycaprolactone microsphere according to the present disclosure can be prepared, for example, using the "solvent extraction/evaporation method", without being limited thereto.

As a specific example of a method for preparing the vitamin C-containing polycaprolactone microsphere according to the present disclosure, such preparation method comprises the steps of: (a) preparing a dispersed phase by dissolving polycaprolactone in a first solvent and dissolving vitamin C in a second solvent to prepare each solution, and then uniformly mixing the two solutions to prepare a single solution, thereby preparing a dispersed phase; (b) preparing an emulsion by mixing the dispersed phase with an aqueous solution (continuous phase) containing a surfactant; (c) forming a microsphere by extracting and evaporating the organic solvent from the dispersed phase into a continuous phase in the emulsion prepared in step (b); and (d) recovering the microsphere from the continuous phase of step (c) to prepare a vitamin C-containing polycaprolactone microsphere.

In step (a), the inherent viscosity of polycaprolactone is preferably in the range of 0.16 to 1.90 dL/g.

The first solvent used for dissolving polycaprolactone in step (a) preferably has properties that are immiscible with water. By utilizing the properties of the organic solvent that are immiscible with water, the dispersed phase can be homogeneously mixed and dispersed in an aqueous solution containing a surfactant that is a continuous phase in step (b) described below, thereby forming an emulsion. The type of the solvent that dissolves polycaprolactone is not particularly limited, and preferably, it may be selected from the group consisting of dichloromethane, chloroform, ethyl acetate, methyl ethyl ketone, and a mixed solvent thereof. More preferably, dichloromethane, ethyl acetate or a mixed solvent thereof can be used.

The second solvent for dissolving vitamin C in step (a) may be selected from the group consisting of dimethyl sulfoxide, methyl alcohol, ethyl alcohol, acetone, acetonitrile, dimethylformamide, N-methylpyrrolidone, acetic acid, and a mixture thereof. Preferably, dimethyl sulfoxide, methyl alcohol or a mixed solvent thereof can be used.

In step (a), a polycaprolactone and a vitamin C solution are mixed to prepare a uniform mixed solution, thereby preparing a dispersed phase. Preferably, the mixed solution of polycaprolactone and vitamin C is homogeneously dissolved. As an example, when using dichloromethane as a solvent for polycaprolactone and using dimethyl sulfoxide as a solvent for vitamin C, the amount of dimethyl sulfoxide used is preferably 3% by weight to 40% by weight relative to the weight of dichloromethane. When the amount of dimethyl sulfoxide is less than 3% by weight, it is highly likely that vitamin C is precipitated due to the decrease of solubility by dichloromethane. When it exceeds 40% by weight, the hydrophobic property of the dispersed phase is reduced, and an excessive amount of dimethyl sulfoxide is rapidly released in the continuous phase, making it difficult to form a dispersed phase in the form of droplets that are not mixed with the continuous phase, which is not preferable.

In step (b), the method for homogeneously mixing the dispersion phase and the aqueous solution containing the surfactant is not particularly limited, and preferably, the mixing can be performed using a high-speed stirrer, an in-line mixer, a membrane emulsification method, a microfluidic emulsification method, or the like.

As an example, when performing the mixing using a membrane emulsification method, the dispersed phase prepared in step (a) is passed through a membrane having uniformly sized micropores and transferred to a continuous phase containing a surfactant to prepare an emulsion.

The type of the surfactant used of step (b) is not particularly limited, and the surfactant can be used without limitation as long as it can help the dispersion phase to form a stable droplet emulsion within the continuous phase. Preferably, the surfactant may be selected from the group consisting of methyl cellulose, polyvinylpyrrolidone, carboxymethylcellulose, lecithin, gelatin, polyvinyl alcohol, polyoxyethylene sorbitan fatty acid ester, polyoxyethylene castor oil derivatives, and mixtures thereof. Most preferably, polyvinyl alcohol can be used.

In step (b), the content of the surfactant in the continuous phase containing the surfactant may be 0.01 w/v % to 20 w/v %, preferably 0.1 w/v % to 5 w/v % based on the total volume of the continuous phase containing the surfactant. When the content of surfactant is less than 0.01 w/v %, a dispersed phase or emulsion in the form of droplets may not be formed in the continuous phase. When the content of surfactant exceeds 20 w/v %, it may be difficult to remove the surfactant after fine particles are formed in the continuous phase due to excessive surfactant. In an embodiment of the present disclosure, the vitamin C-containing polycaprolactone microsphere is prepared using 1 to 5 w/v % of polyvinyl alcohol.

In step (c), when the emulsion comprising a dispersed phase in the form of droplets and a continuous phase containing a surfactant is maintained or stirred at a temperature below the boiling point of the organic solvent for a certain period of time, for example, 2 to 48 hours, the organic solvent can be extracted into a continuous phase from a polycaprolactone-vitamin C solution in the form of a droplet which is the dispersed phase. A part of the organic solvent extracted into the continuous phase can be evaporated from the surface of the continuous phase. As the organic solvent is removed from the solution in the form of droplets, the dispersed phase in the form of droplets is solidified to form microspheres, and thereby, the form of a suspension containing microspheres (microsphere suspension) is obtained.

In step (c), in order to more efficiently remove the organic solvent, the temperature of the continuous phase may be heated for a certain period of time. For example, the stirring can be performed, for example, but not limited thereto, for 48 hours or less, preferably 1 to 36 hours, more preferably for 3 to 24 hours, while maintaining the temperature 5 to 39.6° C., preferably 10 to 35° C., more preferably 15 to 30° C., thereby removing the organic solvent.

In step (d), the method for recovering polycaprolactone microspheres can be performed using several known techniques, and for example, a method such as filtration or centrifugation can be used.

Between steps (c) and (d), the residual surfactant may be removed through filtration and washing, and then filtration may be performed again to recover the microspheres.

The washing step for removing the residual surfactant can be usually performed using water, and the washing step can be repeated several times.

Further, as described above, when the emulsion is formed using the high-speed stirrer and the in-line mixer in step (b), a uniform microsphere can be obtained by additionally using a sieving process between steps (c) and (d). The sieving process can be performed using a known technique, and the microspheres of small particles and large particles can be filtered using a sieve membrane having different sizes to obtain microspheres of uniform size.

According to another aspect of the present disclosure, there is provided a filler comprising the vitamin C-containing polycaprolactone microsphere of the present disclosure; and a pharmaceutically acceptable aqueous carrier and a vitamin C-containing polycaprolactone microsphere.

As the pharmaceutically acceptable aqueous carrier, for example, an aqueous solution for injection such as purified water, physiological saline, or phosphate buffer may be used. Further, the filler may, together with the vitamin C-containing polycaprolactone microsphere and the pharmaceutically acceptable aqueous carrier, include at least one selected from the group consisting of cellulose derivatives such as carboxymethylcellulose (CMC) and hydroxypropylmethylcellulose (HPMC), solutes such as hyaluronic acid, lidocaine, polydeoxyribonucleotide (PDRN), polynucleotide (PN), and lubricants such as glycerin, if necessary, but is not limited thereto. Hyaluronic acid is preferred. When hyaluronic acid is further included and combined, the volume during initial administration may be maintained longer.

In one embodiment, the content of each component included in the filler comprising the vitamin C-containing polycaprolactone microsphere of the present disclosure may be 2 to 50% by weight of the vitamin C-containing polycaprolactone microsphere (the content of vitamin C in the polycaprolactone microparticle is 0.01 to 6% by weight), 15 to 97.9% by weight of the pharmaceutically acceptable aqueous carrier, 0.1 to 5% by weight of the solute and 0 to 48% by weight of the lubricant, based on the total 100% by weight of the filler formulation, but is not limited thereto. When hyaluronic acid is added as a solute, hyaluronic acid having a crosslinking rate of 0 to 5% may be used.

The filler comprising the vitamin C-containing polycaprolactone microsphere according to the present disclosure not only exhibits a rapid collagen-forming effect at the treated site immediately after the treatment, and exhibits a tissue repair property showing a natural and ideal volume feeling, but also maintains the in vivo stability of vitamin C, has good injectability, and exhibits excellent effects for a long period of time, and therefore, can be very usefully used for cosmetic or therapeutic purposes.

As a specific example, the filler including these polycaprolactone microspheres can be used for filling of biological tissues, winkle improvement through filling of wrinkles, remodeling of the face, or restoring or increasing the volume of soft tissues such as lips, nose, buttocks, cheeks or chest. The filler including the polycaprolactone microspheres may be administered in a dosage form suitable for this use, and preferably may be an injection.

In another aspect, the present disclosure provides a pre-filled syringe filled with a filler comprising the polycaprolactone microspheres.

Hereinafter, the present disclosure will be described in more detail by way of examples. However, these examples are for illustrative purposes only, and the scope of the present disclosure is not limited thereto.

Example 1: Preparation of Polycaprolactone Microsphere with Encapsulated Ascorbic Acid The disperse phase was prepared by dissolving 4.9975 g of biocompatible polymer Purasorb PC 04 (manufacturer: Corbion, The Netherlands) and 0.0025 g of ascorbic acid (manufacturer: Tokyo Chemical Industries, Japan) in 19.99 g of dichloromethane (manufacturer: J.T. Baker, USA) and 1.70 mL of dimethyl sulfoxide (manufacturer: Sigma Aldrich, USA), respectively, and mixing the two solutions.

As the continuous phase, a 1 w/v % polyvinyl alcohol aqueous solution (viscosity: 4.8 to 5.8 mPa·s) was used, and 1200 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 1-1: Preparation of Polycaprolactone Microsphere with Encapsulated Ascorbic Acid The disperse phase was prepared by dissolving 4.985 g of biocompatible polymer Purasorb PC 04 (manufacturer: Corbion, The Netherlands) and 0.015 g of ascorbic acid (manufacturer: Tokyo Chemical Industries, Japan) in 19.94 g of dichloromethane (manufacturer: J.T. Baker, USA) and 1.70 mL of dimethyl sulfoxide (manufacturer: Sigma Aldrich, USA), respectively, and mixing the two solutions.

As the continuous phase, a 1 w/v % polyvinyl alcohol aqueous solution (viscosity: 4.8 to 5.8 mPa·s) was used, and 1200 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 1-2: Preparation of Polycaprolactone Microsphere with Encapsulated Ascorbic Acid The disperse phase was prepared by dissolving 4.85 g of biocompatible polymer Purasorb PC 04 (manufacturer: Corbion, The Netherlands) and 0.15 g of ascorbic acid (manufacturer: Tokyo Chemical Industries, Japan) in 19.4 g of dichloromethane (manufacturer: J.T. Baker, USA) and 1.76 mL of dimethyl sulfoxide (manufacturer: Sigma Aldrich, USA), respectively, and mixing the two solutions.

As the continuous phase, a 1 w/v % polyvinyl alcohol aqueous solution (viscosity: 4.8 to 5.8 mPa·s) was used, and 1200 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 1-3: Preparation of Polycaprolactone Microsphere with Encapsulated Ascorbic Acid The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 1-4: Preparation of Polycaprolactone Microsphere with Encapsulated Ascorbic Acid The disperse phase was prepared by dissolving 4.0 g of biocompatible polymer Purasorb PC 04 (manufacturer: Corbion, The Netherlands) and 1.0 g of ascorbic acid (manufacturer: Tokyo Chemical Industries, Japan) in 16 g of dichloromethane (manufacturer: J.T. Baker, USA) and 5.23 mL of dimethyl sulfoxide (manufacturer: Sigma Aldrich, USA), respectively, and mixing the two solutions.

As the continuous phase, a 3 w/v % polyvinyl alcohol aqueous solution (viscosity: 4.8 to 5.8 mPa·s) was used, and 1100 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 2: Preparation of Polycaprolactone Microsphere with Encapsulated Ascorbic Acid The disperse phase was prepared by dissolving 4.5 g of biocompatible polymer Purasorb PC 02 (manufacturer: Corbion, The Netherlands) and 0.5 g of ascorbic acid (manufacturer: Tokyo Chemical Industries, Japan) in 12.85 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1200 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 2-1: Preparation of Polycaprolactone Microsphere with Encapsulated Ascorbic Acid The disperse phase was prepared by dissolving 4.5 g of biocompatible polymer Purasorb PC 12 (manufacturer: Corbion, The Netherlands) and 0.5 g of ascorbic acid (manufacturer: Tokyo Chemical Industries, Japan) in 25 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1500 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 2-2: Preparation of Polycaprolactone Microsphere with Encapsulated Ascorbic Acid The disperse phase was prepared by dissolving 4.5 g of biocompatible polymer Purasorb PC 17 (manufacturer: Corbion, The Netherlands) and 0.5 g of ascorbic acid (manufacturer: Tokyo Chemical Industries, Japan) in 37.5 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 5 w/v % polyvinyl alcohol aqueous solution (viscosity: 4.8 to 5.8 mPa·s) was used, and 2250 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent.

When the removal of the organic solvent was completed, the microsphere suspension was repeatedly washed with distilled water several times to remove and obtain residual polyvinyl alcohol, and the obtained microspheres were lyophilized.

Example 3: Preparation of Polycaprolactone Microsphere with Encapsulated Ascorbic Acid Using High-Speed Stirrer The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was placed in a preparation container, and while stirring the equipped high-speed mixer at a speed of 4500 rpm, the dispersed phase was injected at a flow rate of 7 mL per minute. The microsphere suspension was stirred at a speed of 150 rpm. The temperature of the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 4: Preparation of Polycaprolactone Microsphere with Encapsulated Ascorbic Acid The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a porous membrane having a diameter of 5 µm, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 4-1: Preparation of Polycaprolactone Microsphere with Encapsulated Ascorbic Acid The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a porous membrane having a diameter of 30 µm, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 4-2: Preparation of Polycaprolactone Microsphere with Encapsulated Ascorbic Acid The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a porous membrane having a diameter of 50 µm, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were Lyophilized.

Example 5: Preparation of Polycaprolactone Microsphere with Encapsulated Sodium Ascorbyl Phosphate The disperse phase was prepared by dissolving 4.5 g of biocompatible polymer Purasorb PC 04 (manufacturer: Corbion, The Netherlands) and 0.5 g of sodium ascorbyl phosphate (manufacturer: BASF Care Creations, Germany) in 18 g of dichloromethane (manufacturer: J.T. Baker, USA) and 3.15 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with tertiary distilled water several times to remove and obtain residual polyvinyl alcohol, and the obtained microspheres were lyophilized.

Example 5-1: Preparation of Polycaprolactone Microsphere with Encapsulated Ascorbyl Palmitate The disperse phase was prepared by dissolving 4.5 g of biocompatible polymer Purasorb PC 04 (manufacturer: Corbion, The Netherlands) and 0.5 g of ascorbyl palmitate (manufacturer: Thermo Fisher Scientific, USA) in 18 g of dichloromethane (manufacturer: J.T. Baker, USA) and 1.6 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Example 6: Preparation of Polycaprolactone Microsphere Filler Using Carboxymethylcellulose as a Solute The polycaprolactone microsphere filler was prepared by preparing a solution for the suspension of microspheres and then mixing the microspheres. 2 g of carboxymethylcellulose (manufacturer: Ashland, USA) was added to a phosphate buffer at 75° C., dissolved and cooled with stirring at 100 rpm for 3 hours. When the temperature of the solution reached 25° C., 18 g of glycerin was added thereto and the microspheres prepared in Example 1-3 were mixed at 30% (w/w) to complete the preparation of a polycaprolactone microsphere filler.

Example 6-1: Preparation of Polycaprolactone Microsphere Filler Using Hyaluronic Acid as a Solute The polycaprolactone microsphere filler was prepared by preparing a solution for the suspension of microspheres and then mixing the microspheres. 1 g of hyaluronic acid (manufacturer: Bloomage Freda Biopharm, China) was added to a phosphate buffer at 55° C., dissolved and cooled. When the temperature of the solution reached 25° C., 18 g of glycerin was added thereto and the microspheres prepared in Example 1-3 were mixed at 30% (w/w) to complete the preparation of a polycaprolactone microsphere filler.

Comparative Example 1: Preparation of Polycaprolactone Microspheres

The disperse phase was prepared by mixing 5 g of biocompatible polymer Purasorb PC 04 (manufacturer: Corbion, The Netherlands) with 20 g of dichloromethane (manufacturer: J.T. Baker, USA).

As the continuous phase, a 1 w/v % polyvinyl alcohol aqueous solution (viscosity: 4.8 to 5.8 mPa·s) was used, and 1200 mL of the continuous phase was supplied to an emulsification apparatus equipped with a porous membrane having a diameter of 10 μm, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with tertiary distilled water several times to remove and obtain residual polyvinyl alcohol, and the obtained microspheres were lyophilized.

Comparative Example 1-1: Preparation of Polycaprolactone Microsphere with Encapsulated Ascorbic Acid The disperse phase was prepared by dissolving 3.5 g of biocompatible polymer Purasorb PC 04 (manufacturer: Corbion, The Netherlands) and 1.5 g of ascorbic acid (manufacturer: Tokyo Chemical Industries, Japan) in 14 g of dichloromethane (manufacturer: J.T. Baker, USA) and 9.95 mL of dimethyl sulfoxide (manufacturer: Sigma Aldrich, USA), respectively, and mixing the two solutions.

As the continuous phase, a 3 w/v % polyvinyl alcohol aqueous solution (viscosity: 4.8 to 5.8 mPa·s) was used, and 1000 mL of the continuous phase was supplied to an emulsification apparatus equipped with a 10 μm diameter porous membrane, and at the same time, the prepared dispersed phase was injected to prepare a microsphere. The prepared microsphere suspension was placed in a preparation container and stirred at a speed of 150 rpm. The temperature of the membrane emulsification apparatus and the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Comparative Example 2: Preparation of Polycaprolactone Microsphere with Encapsulated Ascorbic Acid Using High-Speed Stirrer The disperse phase was prepared by dissolving 4.5 g of biocompatible polymer Purasorb PC 04 (manufacturer: Corbion, The Netherlands) and 0.5 g of ascorbic acid (manufacturer: Tokyo Chemical Industries, Japan) in 18 g of dichloromethane (manufacturer: J.T. Baker, USA) and 2.95 mL of dimethyl sulfoxide (manufacturer: Sigma Aldrich, USA), respectively, and mixing the two solutions.

As the continuous phase, a 2 w/v % polyvinyl alcohol aqueous solution (viscosity: 4.8 to 5.8 mPa·s) was used, and 1100 mL of the continuous phase was placed in a preparation container, and while stirring the equipped high-speed mixer at a speed of 4500 rpm, the dispersed phase was injected at a flow rate of 7 mL per minute. The microsphere suspension was stirred at a speed of 150 rpm. The temperature of the preparation container was maintained at 25° C.

When the injection of the dispersed phase was completed, the microsphere suspension was stirred at 25° C. for 12 hours at a speed of 150 rpm to remove the organic solvent. When the removal of the organic solvent was completed, the microsphere suspension was repeatedly washed with distilled water several times to remove and obtain residual polyvinyl alcohol, and the obtained microspheres were lyophilized.

Comparative Example 3: Preparation of Polycaprolactone Microsphere Filler Using Carboxymethylcellulose as a Solute The polycaprolactone microsphere filler was prepared by preparing a solution for the suspension of microspheres and then mixing the microspheres. 2 g of carboxymethylcellulose (manufacturer: Ashland, USA) was added to a phosphate buffer at 75° C., dissolved and cooled with stirring at 100 rpm for 3 hours. When the temperature of the solution reached 25° C., 18 g of glycerin was added thereto and the microspheres prepared in Comparative Examples 1 were mixed at 30% (w/w) to complete the preparation of a polycaprolactone microsphere filler.

Comparative Example 3-1: Preparation of Polycaprolactone Microsphere Filler Using Hyaluronic Acid as a Solute The polycaprolactone microsphere filler was prepared by preparing a solution for the suspension of microspheres and then mixing the microspheres. 1 g of hyaluronic acid (manufacturer: Bloomage Freda Biopharm, China) was added to a phosphate buffer at 55° C., dissolved and cooled. When the temperature of the solution reached 25° C., 18 g of glycerin was added thereto and the microspheres prepared in Comparative Example 1 were mixed at 30% (w/w) to complete the preparation of a polycaprolactone microsphere filler.

Experimental Example 1: Observation of Microsphere Morphology Using Optical Microscope For morphological analysis of microspheres, the morphology of the microspheres prepared in Example 1-4 and Comparative Example 1-1 was observed using an optical microscope. Specifically, the microsphere suspension was dropped on a slide glass, and the slide glass was placed on an optical microscope stage (manufacturer: Olympus BH-2, Japan), and the microsphere morphology was observed at ×100 magnification (objective lens ×10, ocular lens ×10).

Figure 1A:
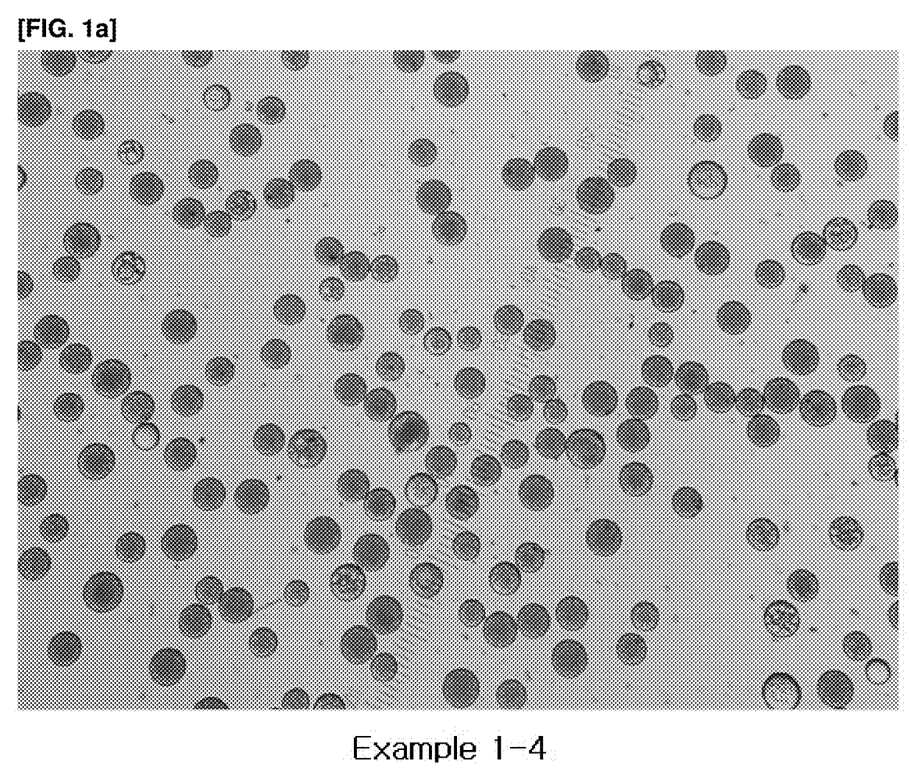
FIG. 1a is a photograph of the shape of the ascorbic acid-containing polycaprolactone microsphere prepared according to Example 1-4, taken by an optical microscope. As can be seen from the photograph, it can be confirmed that the produced microspheres maintain a spherical shape even while having a porous morphological characteristic on the surface.
Figure 1B:
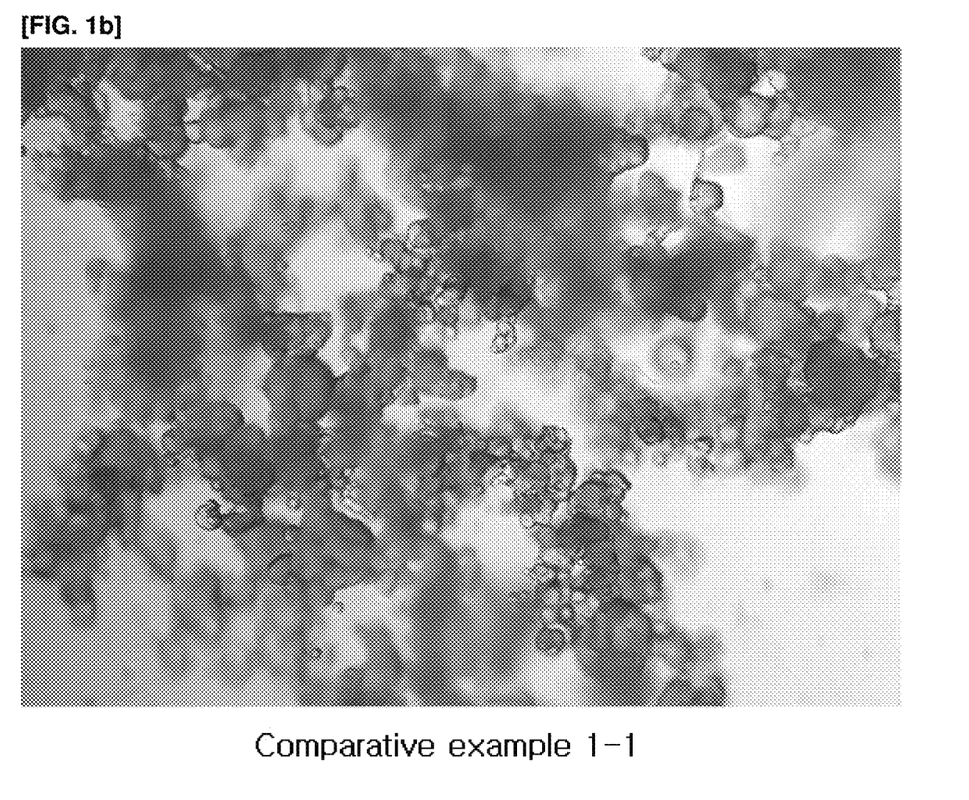
FIG. 1b is a photograph of the shape of the ascorbic acid-containing polycaprolactone microsphere prepared by using excess ascorbic acid according to Comparative Example 1-1, taken by an optical microscope. The produced microspheres do not maintain a spherical shape and exhibit a morphological characteristic that microspheres are agglomerated or broken

As shown in FIGS. 1A and 1B, the microsphere of Example 1-4 maintained a spherical shape while having a porous morphological characteristic on the microsphere surface, whereas the microsphere of Comparative Example 1-1 did not maintain a spherical shape and could observe the morphological characteristics of agglomerated or broken microspheres. This was predicted that excess dimethylsulfoxide used in Comparative Example 1-1 was rapidly released into the continuous phase to thereby reduce the dispersed phase properties that was not mixable with the continuous phase, making it difficult to maintain intact microspheres.

Experimental Example 2: Particle Size Analysis of Microsphere Using a Laser Diffraction Method This experiment was carried out to quantitatively measure the average particle size and distribution of microspheres and confirm the uniformity of particles. The experimental procedure is as follows.

50 mg of microspheres were mixed with 1 mL of ultrapure water, mixed with a vortex mixer for 20 seconds, then placed in an ultrasonic generator for 1 minute and dispersed. The microsphere dispersion was placed in a particle size analyzer (Microtrac Bluewave, Japan) and measured for 20 seconds. As an index of particle size uniformity, the span value was determined by the following Formula.

$$\text{Span Value} = (D_{v,0.9} - D_{v,0.1})/D_{v,0.5} \qquad \text{[Formula 1]}$$

TABLE 1

|  | $D_{v,0.5}$ (μm) | Span Value |
|---|---|---|
| Example 1 | 36.7 | 0.61 |
| Example 1-1 | 36.2 | 0.60 |
| Example 1-2 | 36.8 | 0.62 |
| Example 1-3 | 35.6 | 0.66 |
| Example 1-4 | 35.4 | 0.73 |
| Example 2 | 34.8 | 0.62 |
| Example 2-1 | 35.1 | 0.65 |
| Example 2-2 | 37.3 | 0.64 |
| Example 3 | 32.7 | 0.92 |
| Example 4 | 13.9 | 0.59 |
| Example 4-1 | 62.8 | 0.69 |
| Example 4-2 | 101.8 | 0.73 |
| Example 5 | 36.2 | 0.61 |
| Example 5-1 | 36.4 | 0.63 |
| Comparative Example 1 | 35.2 | 0.58 |
| Comparative Example 2 | 30.1 | 1.43 |

As shown in Table 1, the microspheres of Example 1, Example 1-1, Example 1-2, Example 1-3, Example 1-4, and Comparative Example 1 were respectively prepared using various amounts of ascorbic acid, but had the average particle size of about 35 μm which was a similar particle size. Therefore, it was confirmed that ascorbic acid used for preparing the dispersed phase did not significantly affect the particle size.

In Example 4, Example 4-1 and Example 4-2, it was confirmed that the particle size could be adjusted according to the change in the porous membrane equipped with the emulsification apparatus.

Examples 1-3 and Comparative Example 2 had a difference in the method of homogeneously mixing the dispersed phase and the aqueous solution containing the surfactant in the process of preparing the microspheres, and the microspheres prepared therefrom showed different average particle sizes and span values. In more detail, the microsphere of Comparative Example 2 was the microsphere prepared using a high-speed stirrer, confirming that the average particle size was relatively reduced compared to Example 1-3 and the span value was 1.43 having a wide particle size distribution.

Experimental Example 3: Analysis of Ascorbic Acid Encapsulated in Polycaprolactone Microspheres This experiment was performed using high performance liquid chromatography for quantitative analysis of ascorbic acid encapsulated in polycaprolactone microspheres. The detailed experimental procedure is as follows.

The mobile phase used in the high performance liquid chromatography allowed a 40 v/v % acetonitrile solution containing 0.1 v/v % trichloroacetic acid to flow at a flow rate of 0.5 mL/min, and a column filled with C18 filler (Inertsil ODS-3, 5 um, 4.5×150 mm, manufactured by GL Science, Japan). 10 mg of microspheres were diluted in a mixture of N-methylpyrrolidone and acetonitrile (8:2, v/v), injected into high performance liquid chromatography, and measured using a UV absorbance detector at a wavelength of 245 nm.

TABLE 2

|  | Encapsulation amount (wt %) |
|---|---|
| Example 1 | 0.02 |
| Example 1-1 | 0.13 |
| Example 1-2 | 1.02 |
| Example 1-3 | 3.24 |
| Example 1-4 | 5.60 |
| Comparative Example 1-1 | 7.54 |

As shown in Table 2 above, it was confirmed that in Example 1, Example 1-1, Example 1-2, Example 1-3, and Example 1-4, the content also increased in proportion to the increase in the amount of ascorbic acid used in the preparation of the dispersed phase. In particular, Example 1-4 showed that the maximum encapsulation amount of ascorbic acid was 5.60% by weight while maintaining the shape of intact microspheres.

On the other hand, Comparative Example 1-1 showed 7.54% by weight, a relatively higher encapsulation amount of ascorbic acid, but it was confirmed that there was a phenomenon that the shape of the microspheres are non-uniform and are entangled/adhered, and thus, they are not suitable as the encapsulation and delivery agent of ascorbic acid.

Experimental Example 4: Persistence Evaluation of Polycaprolactone Microsphere Filler In this experiment, the volume was analyzed after filler administration to experimental animals to evaluate the persistence of polycaprolactone microsphere fillers.

The polycaprolactone microsphere fillers were prepared as in Example 6, Example 6-1, Comparative Example 3 and Comparative Example 3-1, and injected subcutaneously in 100 μL increments to SKH1-Hrhr hairless mice at 6 weeks after birth, and the volume analysis of the administered site was performed for a predetermined period (1 week, 4 weeks, and 8 weeks immediately after administration). PRIMOS$^{LITE}$ (GFMesstechnikGmbH, Germany) was used for the volume measurement, and PRIMOS 5.6 was used as the analysis program.

TABLE 3

|  | Immediately after administration | 1 week | 4 weeks | 8 weeks |
|---|---|---|---|---|
| Example 6 | 100 | 94 | 88 | 79 |
| Example 6-1 | 101 | 114 | 106 | 100 |
| Comparative Example 3 | 100% | 64% | 62% | 58% |
| Comparative Example 3-1 | 102% | 86% | 83 | 81 |

As shown in Table 3 above, it was confirmed that in Example 6 and Example 6-1, there was a difference in the volume change depending on the filler composition for an injection. It was confirmed that the hyaluronic acid used in Example 6-1 was relatively more effective in maintaining the volume than carboxymethylcellulose.

As shown in the results of Example 6-1 and Comparative Example 3-1, it was confirmed that in the case of Example 6-1 in which microspheres with encapsulated ascorbic acid were used, the volume reduction was relatively small for 8 weeks after administration, and the increase phenomenon of the initial volume was observed. This was predicted to allow ascorbic acid encapsulated in the microspheres to promote various biological functions such as the production of hyaluronic acid and synthesis of collagen.

The invention claimed is:

1. A polycaprolactone microsphere comprising 0.01 to 6.5% by weight of vitamin C based on total 100% by weight of the polycaprolactone microsphere containing vitamin C, and having an average particle size of 10 to 100 μm,
    wherein the polycaprolactone has an intrinsic viscosity of 0.16 to 1.90 dL/g, measured in chloroform at 25° C. using a Ubbelohde viscometer;
    the vitamin C is encapsulated in said polycaprolactone microsphere; and
    the microsphere has a span value of 1.0 or less.

2. The polycaprolactone microsphere according to any one of claim 1, wherein the vitamin C is at least one selected from the group consisting of L-ascorbic acid, sodium ascorbylphosphate, magnesium ascorbylphosphate, calsium ascorbylphosphate, ascorbic acid polypeptide, ethyl ascorbyl ether, ascorbyl dipalmitate, ascorbyl palmitate, ascorbyl glucoside and ascorbyl ethylsilanol pectinate.

3. A method for preparing a vitamin C-containing polycaprolactone microsphere, comprising the steps of:
    (a) preparing a dispersed phase by dissolving polycaprolactone in a first solvent and dissolving vitamin C in a second solvent to prepare each solution, and then uniformly mixing the two solutions to prepare a single solution;
    (b) preparing an emulsion by mixing the dispersed phase with an aqueous solution (continuous phase) containing a surfactant;
    (c) forming a microsphere by extracting and evaporating the organic solvent from the dispersed phase into a continuous phase in the emulsion prepared in step (b); and
    (d) recovering the microsphere from the continuous phase of step (c) to prepare a polycaprolactone microsphere,
    wherein the polycaprolactone has an intrinsic viscosity of 0.16 to 1.90 dL/g, measured in chloroform at 25° C. using a Ubbelohde viscometer;
    the vitamin C is encapsulated in said polycaprolactone microsphere; and
    the microsphere has a span value of 1.0 or less.

4. The method for preparing a polycaprolactone microsphere according to claim 3, wherein the vitamin C is at least one selected from the group consisting of L-ascorbic acid, sodium ascorbylphosphate, magnesium ascorbylphosphate, calsium ascorbylphosphate, ascorbic acid polypeptide, ethyl ascorbyl ether, ascorbyl dipalmitate, ascorbyl palmitate, ascorbyl glucoside and ascorbyl ethylsilanol pectinate.

5. The method for preparing a polycaprolactone microsphere according to claim 3, wherein the first solvent of step (a) is at least one selected from the group consisting of dichloromethane, chloroform, ethyl acetate, methyl ethyl ketone, and a mixed solvent thereof.

6. The method for preparing a polycaprolactone microsphere according to claim 3, wherein the second solvent of step (a) is at least one selected from the group consisting of dimethyl sulfoxide, methyl alcohol, ethyl alcohol, acetone, acetonitrile, dimethylformamide, N-methylpyrrolidone, acetic acid, and a mixture thereof.

7. The method for preparing a polycaprolactone microsphere according to claim 3, wherein the surfactant of step (b) is at least one selected from the group consisting of methyl cellulose, polyvinylpyrrolidone, carboxymethylcellulose, lecithin, gelatin, polyvinyl alcohol, polyoxyethylene sorbitan fatty acid ester, polyoxyethylene castor oil derivatives, and mixtures thereof.

8. The method for preparing a polycaprolactone microsphere according to claim 3, wherein the surfactant of step (b) is contained in an amount of 0.01 w/v % to 20 w/v % based on the total volume of the aqueous solution containing the surfactant.

9. A polycaprolactone microsphere filler comprising 2 to 50% by weight of a vitamin C-containing polycaprolactone microsphere which comprises 0.01 to 6.5% by weight of the vitamin C based on the total weight of the microsphere and has an average particle size of 10 to 100 μm; 0.1 to 5% by weight of a solute; 0 to 48% by weight of a lubricant; and 15 to 97.9% by weight of a pharmaceutically acceptable aqueous carrier, based on total 100% by weight of the polycaprolactone microsphere filler,
wherein the polycaprolactone has an intrinsic viscosity of 0.16 to 1.90 dL/g, measured in chloroform at 25° C. using a Ubbelohde viscometer;
the vitamin C is encapsulated in said polycaprolactone microsphere; and
the microsphere has a span value of 1.0 or less.

10. The polycaprolactone microsphere filler according to claim 9, wherein the vitamin C is at least one selected from the group consisting of L-ascorbic acid, sodium ascorbylphosphate, magnesium ascorbylphosphate, calsium ascorbylphosphate, ascorbic acid polypeptide, ethyl ascorbyl ether, ascorbyl dipalmitate, ascorbyl palmitate, ascorbyl glucoside and ascorbyl ethylsilanol pectinate.

11. The polycaprolactone microsphere filler according to claim 9, wherein the solute is at least one selected from the group consisting of carboxymethylcellulose (CMC), hydroxypropylmethylcellulose (HPMC), hyaluronic acid, lidocaine, polydeoxyribonucleotide (PDRN), polynucleotide (PN), and a mixture thereof.

12. The polycaprolactone microsphere filler according to claim 9, wherein the lubricant is glycerin.

13. The polycaprolactone microsphere filler according to claim 9, wherein the pharmaceutically acceptable aqueous carrier is distilled water, physiological saline, or phosphate buffer.

14. The polycaprolactone microsphere filler according to claim 9, wherein the filler is for improving wrinkles, repairing soft tissues or expanding volume, or correcting contours.

15. The polycaprolactone microsphere filler according to claim 9, wherein the filler is for an injection.

16. A prefilled syringe filled with the polycaprolactone microsphere filler of claim 1.

* * * * *